United States Patent
Lin

(10) Patent No.: US 9,833,146 B2
(45) Date of Patent: Dec. 5, 2017

(54) SURGICAL SYSTEM AND METHOD OF USE OF THE SAME

(75) Inventor: Andy S. Lin, Boulder, CO (US)

(73) Assignee: COVIDIEN LP, Mansfield, MA (US)

(*) Notice: Subject to any disclaimer, the term of this patent is extended or adjusted under 35 U.S.C. 154(b) by 98 days.

(21) Appl. No.: 13/448,754

(22) Filed: Apr. 17, 2012

(65) Prior Publication Data

US 2013/0274727 A1    Oct. 17, 2013

(51) Int. Cl.
*A61B 18/18*    (2006.01)
*A61B 5/00*    (2006.01)
*A61B 18/22*    (2006.01)
*A61B 18/00*    (2006.01)
*A61B 17/00*    (2006.01)

(52) U.S. Cl.
CPC .......... *A61B 5/0082* (2013.01); *A61B 5/4836* (2013.01); *A61B 18/22* (2013.01); *A61B 2017/00115* (2013.01); *A61B 2018/00577* (2013.01); *A61B 2018/00589* (2013.01); *A61B 2018/00601* (2013.01); *A61B 2018/00642* (2013.01); *A61B 2018/00702* (2013.01); *A61B 2018/00779* (2013.01); *A61B 2018/2244* (2013.01); *A61B 2505/05* (2013.01)

(58) Field of Classification Search
CPC .......... A61N 2005/0632; A61B 5/0082; A61B 5/4836; A61B 18/22
USPC .................................... 606/1–19; 607/88–94
See application file for complete search history.

(56) References Cited

U.S. PATENT DOCUMENTS

| | | | |
|---|---|---|---|
| 3,638,640 A | 2/1972 | Shaw | |
| 4,223,680 A | 9/1980 | Jöbsis | |
| 4,281,645 A | 8/1981 | Jöbsis | |
| 4,321,930 A | 3/1982 | Jöbsis et al. | |
| 4,589,404 A * | 5/1986 | Barath | A61B 1/042 348/359 |
| 4,682,594 A * | 7/1987 | Mok | 606/7 |
| 4,714,341 A | 12/1987 | Hamaguri et al. | |
| 4,805,623 A | 2/1989 | Jöbsis | |
| 4,807,631 A | 2/1989 | Hersh et al. | |
| 4,911,167 A | 3/1990 | Corenman et al. | |
| 4,913,150 A | 4/1990 | Cheung et al. | |
| 4,936,679 A | 6/1990 | Mersch | |
| 4,938,218 A | 7/1990 | Goodman et al. | |
| 4,971,062 A | 11/1990 | Hasebe et al. | |

(Continued)

FOREIGN PATENT DOCUMENTS

| | | |
|---|---|---|
| AU | 732799 | 5/2001 |
| DE | 69123448 | 5/1997 |

(Continued)

*Primary Examiner* — John R Downey

(57) ABSTRACT

A surgical system configured for treating tissue is provided. The surgical system includes a laser source and a laser scalpel. The laser scalpel is adapted to couple to the laser source and is operable in two modes of operation, a first mode of operation to analyze tissue of interest and a second mode of operation to treat tissue of interest. The laser scalpel includes a housing having first and second fiber optic cables extending therethrough. Each of the first and second fiber optic cables operable under the first mode of operation to collect information pertaining to at least one optical property of tissue of interest and at least one of the first and second fiber optic cables also operable under the second mode of operation to treat the tissue of interest.

8 Claims, 1 Drawing Sheet

(56) References Cited

U.S. PATENT DOCUMENTS

| | | | |
|---|---|---|---|
| 4,972,331 A | 11/1990 | Chance | |
| 4,974,591 A | 12/1990 | Awazu et al. | |
| 5,028,787 A | 7/1991 | Rosenthal et al. | |
| 5,065,749 A | 11/1991 | Hasebe et al. | |
| 5,084,327 A | 1/1992 | Stengel | |
| 5,088,493 A | 2/1992 | Giannini et al. | |
| 5,119,815 A | 6/1992 | Chance | |
| 5,122,974 A | 6/1992 | Chance | |
| 5,167,230 A | 12/1992 | Chance | |
| 5,190,038 A | 3/1993 | Polson et al. | |
| 5,246,003 A | 9/1993 | DeLonzor | |
| 5,247,931 A | 9/1993 | Norwood | |
| 5,263,244 A | 11/1993 | Centa et al. | |
| 5,275,159 A | 1/1994 | Griebel | |
| 5,279,295 A | 1/1994 | Martens et al. | |
| 5,297,548 A | 3/1994 | Pologe | |
| 5,355,880 A | 10/1994 | Thomas et al. | |
| 5,372,136 A | 12/1994 | Steuer et al. | |
| 5,385,143 A | 1/1995 | Aoyagi | |
| 5,390,670 A | 2/1995 | Centa et al. | |
| 5,413,099 A | 5/1995 | Schmidt et al. | |
| 5,451,220 A * | 9/1995 | Ciervo | 606/1 |
| 5,469,845 A | 11/1995 | DeLonzor et al. | |
| 5,482,036 A | 1/1996 | Diab et al. | |
| 5,483,646 A | 1/1996 | Uchikoga | |
| 5,495,541 A * | 2/1996 | Murray | A61B 18/24 |
| | | | 385/117 |
| 5,497,769 A | 3/1996 | Gratton et al. | |
| 5,553,614 A | 9/1996 | Chance | |
| 5,555,885 A | 9/1996 | Chance | |
| 5,564,417 A | 10/1996 | Chance | |
| 5,575,285 A | 11/1996 | Takanashi et al. | |
| 5,611,337 A | 3/1997 | Bukta | |
| 5,630,413 A | 5/1997 | Thomas et al. | |
| 5,645,059 A | 7/1997 | Fein et al. | |
| 5,645,060 A | 7/1997 | Yorkey | |
| 5,653,706 A * | 8/1997 | Zavislan et al. | 606/9 |
| 5,680,857 A | 10/1997 | Pelikan et al. | |
| 5,692,503 A | 12/1997 | Keunstner | |
| 5,730,124 A | 3/1998 | Yamauchi | |
| 5,758,644 A | 6/1998 | Diab et al. | |
| 5,779,631 A | 7/1998 | Chance | |
| 5,782,757 A | 7/1998 | Diab et al. | |
| 5,785,703 A * | 7/1998 | Goodman et al. | 606/10 |
| 5,786,592 A | 7/1998 | Hök | |
| 5,830,136 A | 11/1998 | DeLonzor et al. | |
| 5,830,139 A | 11/1998 | Abreu | |
| 5,831,598 A | 11/1998 | Kauffert et al. | |
| 5,842,981 A | 12/1998 | Larsen et al. | |
| 5,871,442 A | 2/1999 | Madarasz et al. | |
| 5,873,821 A | 2/1999 | Chance et al. | |
| 5,920,263 A | 7/1999 | Huttenhoff et al. | |
| 5,995,855 A | 11/1999 | Kiani et al. | |
| 5,995,856 A | 11/1999 | Mannheimer et al. | |
| 5,995,859 A | 11/1999 | Takahashi | |
| 6,011,986 A | 1/2000 | Diab et al. | |
| 6,064,898 A | 5/2000 | Aldrich | |
| 6,081,742 A | 6/2000 | Amano et al. | |
| 6,088,607 A | 7/2000 | Diab et al. | |
| 6,120,460 A | 9/2000 | Abreu | |
| 6,134,460 A | 10/2000 | Chance | |
| 6,150,951 A | 11/2000 | Olejniczak | |
| 6,154,667 A | 11/2000 | Miura et al. | |
| 6,163,715 A | 12/2000 | Larsen et al. | |
| 6,181,958 B1 | 1/2001 | Steuer et al. | |
| 6,181,959 B1 | 1/2001 | Schöllermann et al. | |
| 6,192,260 B1 | 2/2001 | Chance | |
| 6,192,261 B1 | 2/2001 | Gratton et al. | |
| 6,230,035 B1 | 5/2001 | Aoyagi et al. | |
| 6,266,546 B1 | 7/2001 | Steuer et al. | |
| 6,285,895 B1 | 9/2001 | Ristolainen et al. | |
| 6,312,393 B1 | 11/2001 | Abreu | |
| 6,322,515 B1 | 11/2001 | Goor et al. | |
| 6,352,502 B1 | 3/2002 | Chaiken et al. | |
| 6,353,750 B1 | 3/2002 | Kimura et al. | |
| 6,397,091 B2 | 5/2002 | Diab et al. | |
| 6,415,236 B2 | 7/2002 | Kobayashi et al. | |
| 6,419,671 B1 | 7/2002 | Lemberg | |
| 6,438,399 B1 | 8/2002 | Kurth | |
| 6,461,305 B1 | 10/2002 | Schnall | |
| 6,466,809 B1 | 10/2002 | Riley | |
| 6,487,439 B1 | 11/2002 | Skladnev et al. | |
| 6,501,974 B2 | 12/2002 | Huiku | |
| 6,501,975 B2 | 12/2002 | Diab et al. | |
| 6,516,209 B2 | 2/2003 | Cheng et al. | |
| 6,526,301 B2 | 2/2003 | Larsen et al. | |
| 6,544,193 B2 | 4/2003 | Abreu | |
| 6,546,267 B1 | 4/2003 | Sugiura et al. | |
| 6,549,795 B1 | 4/2003 | Chance | |
| 6,580,086 B1 | 6/2003 | Schulz et al. | |
| 6,591,122 B2 | 7/2003 | Schmitt | |
| 6,594,513 B1 | 7/2003 | Jöbsis et al. | |
| 6,606,509 B2 | 8/2003 | Schmitt | |
| 6,606,511 B1 | 8/2003 | Ali et al. | |
| 6,615,064 B1 | 9/2003 | Aldrich | |
| 6,618,042 B1 | 9/2003 | Powell | |
| 6,622,095 B2 | 9/2003 | Kobayashi et al. | |
| 6,654,621 B2 | 11/2003 | Palatnik et al. | |
| 6,654,624 B2 | 11/2003 | Diab et al. | |
| 6,658,276 B2 | 12/2003 | Kianl et al. | |
| 6,658,277 B2 | 12/2003 | Wasserman | |
| 6,662,030 B2 | 12/2003 | Khalil et al. | |
| 6,668,183 B2 | 12/2003 | Hicks et al. | |
| 6,671,526 B1 | 12/2003 | Aoyagi et al. | |
| 6,671,528 B2 | 12/2003 | Steuer et al. | |
| 6,675,029 B2 | 1/2004 | Monfre et al. | |
| 6,678,543 B2 | 1/2004 | Diab et al. | |
| 6,681,128 B2 | 1/2004 | Steuer et al. | |
| 6,684,090 B2 | 1/2004 | Ali et al. | |
| 6,687,519 B2 | 2/2004 | Steuer et al. | |
| 6,690,958 B1 | 2/2004 | Walker et al. | |
| 6,697,658 B2 | 2/2004 | Al-Ali | |
| 6,708,048 B1 | 3/2004 | Chance | |
| 6,711,424 B1 | 3/2004 | Fine et al. | |
| 6,711,425 B1 | 3/2004 | Reuss | |
| 6,714,245 B1 | 3/2004 | Ono | |
| 6,731,274 B2 | 5/2004 | Powell | |
| 6,785,568 B2 | 8/2004 | Chance | |
| 6,793,654 B2 | 9/2004 | Lemberg | |
| 6,801,648 B2 | 10/2004 | Cheng | |
| 6,801,797 B2 | 10/2004 | Mannheimer et al. | |
| 6,801,798 B2 | 10/2004 | Geddes et al. | |
| 6,801,799 B2 | 10/2004 | Mendelson | |
| 6,829,496 B2 | 12/2004 | Nagai et al. | |
| 6,850,053 B2 | 2/2005 | Daalmans et al. | |
| 6,859,658 B1 | 2/2005 | Krug | |
| 6,863,652 B2 | 3/2005 | Huang et al. | |
| 6,873,865 B2 | 3/2005 | Steuer et al. | |
| 6,889,153 B2 | 5/2005 | Dietiker | |
| 6,898,451 B2 | 5/2005 | Wuori | |
| 6,939,307 B1 | 9/2005 | Dunlop | |
| 6,947,780 B2 | 9/2005 | Scharf | |
| 6,949,081 B1 | 9/2005 | Chance | |
| 6,961,598 B2 | 11/2005 | Diab | |
| 6,983,178 B2 | 1/2006 | Fine et al. | |
| 6,993,371 B2 | 1/2006 | Kiani et al. | |
| 6,996,427 B2 | 2/2006 | Ali et al. | |
| 7,006,676 B1 | 2/2006 | Zeylikovich et al. | |
| 7,024,235 B2 | 4/2006 | Melker et al. | |
| 7,027,849 B2 | 4/2006 | Al-Ali | |
| 7,027,850 B2 | 4/2006 | Wasserman | |
| 7,030,749 B2 | 4/2006 | Al-Ali | |
| 7,035,697 B1 | 4/2006 | Brown | |
| 7,041,063 B2 | 5/2006 | Abreu | |
| 7,043,289 B2 | 5/2006 | Fine et al. | |
| 7,047,056 B2 | 5/2006 | Hannula et al. | |
| 7,060,035 B2 | 6/2006 | Wasserman | |
| 7,065,392 B2 | 6/2006 | Kato | |
| 7,090,648 B2 | 8/2006 | Sackner et al. | |
| 7,095,491 B2 | 8/2006 | Forstner et al. | |
| 7,127,278 B2 | 10/2006 | Melker et al. | |
| 7,130,672 B2 | 10/2006 | Pewzner et al. | |
| 7,162,306 B2 | 1/2007 | Caby et al. | |
| 7,164,938 B2 | 1/2007 | Geddes et al. | |

(56) References Cited

U.S. PATENT DOCUMENTS

| | | |
|---|---|---|
| 7,209,775 B2 | 4/2007 | Bae et al. |
| 7,225,005 B2 | 5/2007 | Kaufman et al. |
| 7,236,811 B2 | 6/2007 | Schmitt |
| 7,236,813 B2 | 6/2007 | Parker |
| 7,239,902 B2 | 7/2007 | Schmitt et al. |
| 7,251,518 B2 | 7/2007 | Herrmann |
| 7,257,433 B2 | 8/2007 | Takamura et al. |
| 7,263,395 B2 | 8/2007 | Chan et al. |
| 7,272,426 B2 | 9/2007 | Schmid |
| 7,277,741 B2 | 10/2007 | Debreczeny et al. |
| 7,330,746 B2 | 2/2008 | Demuth et al. |
| 7,343,186 B2 | 3/2008 | Lamego et al. |
| 7,373,193 B2 | 5/2008 | Al/Ali et al. |
| 7,375,347 B2 | 5/2008 | Colvin et al. |
| 7,378,954 B2 | 5/2008 | Wendt |
| 7,469,158 B2 | 12/2008 | Cutler et al. |
| 7,548,771 B2 | 6/2009 | Mannheimer |
| 7,551,950 B2 | 6/2009 | Cheng |
| 7,621,877 B2 | 11/2009 | Schnall |
| 7,689,259 B2 | 3/2010 | Mannheimer et al. |
| 7,904,139 B2 | 3/2011 | Chance |
| 7,979,102 B2 | 7/2011 | Hannula et al. |
| 8,046,059 B2 | 10/2011 | Cho et al. |
| 8,078,246 B2 | 12/2011 | Mannheimer et al. |
| 8,082,015 B2 | 12/2011 | Yodh et al. |
| 8,108,022 B2 | 1/2012 | Balberg et al. |
| 8,126,524 B2 | 2/2012 | Balberg et al. |
| 8,229,529 B2 | 7/2012 | Schmitt |
| 8,255,029 B2 | 8/2012 | Addison et al. |
| 2002/0042558 A1 | 4/2002 | Mendelson |
| 2002/0156354 A1 | 10/2002 | Larson |
| 2002/0198443 A1 | 12/2002 | Ting |
| 2003/0023140 A1 | 1/2003 | Chance |
| 2004/0039379 A1* | 2/2004 | Viator et al. .......... 606/9 |
| 2004/0162548 A1* | 8/2004 | Reiser ........... A61B 18/24 606/7 |
| 2005/0113651 A1 | 5/2005 | Wood et al. |
| 2005/0113656 A1 | 5/2005 | Chance |
| 2005/0177034 A1 | 8/2005 | Beaumont |
| 2005/0192488 A1 | 9/2005 | Bryenton et al. |
| 2005/0209516 A1 | 9/2005 | Fraden |
| 2005/0228248 A1 | 10/2005 | Dietiker |
| 2005/0267346 A1 | 12/2005 | Faber et al. |
| 2006/0052680 A1 | 3/2006 | Diab |
| 2006/0052709 A1* | 3/2006 | DeBaryshe et al. .......... 600/476 |
| 2006/0129038 A1 | 6/2006 | Zelenchuk et al. |
| 2006/0247501 A1 | 11/2006 | Ali |
| 2007/0093702 A1 | 4/2007 | Yu et al. |
| 2008/0139908 A1 | 6/2008 | Kurth |
| 2008/0312533 A1 | 12/2008 | Balberg et al. |
| 2009/0281536 A1* | 11/2009 | Beckman et al. ........... 606/33 |
| 2009/0287197 A1* | 11/2009 | Hanley et al. .......... 606/15 |
| 2010/0081899 A1 | 4/2010 | McKenna |
| 2011/0071373 A1 | 3/2011 | Li |
| 2011/0077485 A1 | 3/2011 | Baker |
| 2011/0082526 A1* | 4/2011 | Rizoiu et al. .......... 607/89 |
| 2011/0160713 A1* | 6/2011 | Neuberger .......... 606/15 |
| 2013/0030267 A1* | 1/2013 | Lisogurski et al. .......... 600/324 |

FOREIGN PATENT DOCUMENTS

| | | |
|---|---|---|
| DE | 19640807 | 9/1997 |
| EP | 0194105 | 9/1986 |
| JP | 3124073 | 5/1991 |
| JP | 3170866 | 7/1991 |
| JP | 3238813 | 10/1991 |
| JP | 4191642 | 7/1992 |
| JP | 4332536 | 11/1992 |
| JP | 5049624 | 3/1993 |
| JP | 7124138 | 5/1995 |
| JP | 10216115 | 9/1998 |
| JP | 11019074 | 1/1999 |
| JP | 2003194714 | 7/2003 |
| JP | 2003210438 | 7/2003 |
| JP | 2003275192 | 9/2003 |
| JP | 2003339678 | 12/2003 |
| JP | 2004008572 | 1/2004 |
| JP | 2004194908 | 7/2004 |
| JP | 2004202190 | 7/2004 |
| JP | 2004248819 | 9/2004 |
| JP | 2004290544 | 10/2004 |
| JP | 2004290545 | 10/2004 |
| WO | WO 9101678 | 2/1991 |
| WO | WO 9200513 | 1/1992 |
| WO | WO 9221281 | 12/1992 |
| WO | WO 9309711 | 5/1993 |
| WO | WO 9313706 | 7/1993 |
| WO | WO 93/16629 | 9/1993 |
| WO | WO 9403102 | 2/1994 |
| WO | WO 9512349 | 5/1995 |
| WO | WO 9749330 | 12/1997 |
| WO | WO 9817174 | 5/1998 |
| WO | WO 98/42249 | 10/1998 |
| WO | WO 98/42251 | 10/1998 |
| WO | WO 9843071 | 10/1998 |
| WO | WO 9932030 | 7/1999 |
| WO | WO 0021438 | 4/2000 |
| WO | WO 0140776 | 6/2001 |
| WO | WO 03077750 | 9/2003 |
| WO | WO 2004010844 | 2/2004 |
| WO | WO 2005009221 | 2/2005 |
| WO | WO 2005064314 | 7/2005 |
| WO | WO 2007051066 | 5/2007 |

\* cited by examiner

SURGICAL SYSTEM AND METHOD OF USE OF THE SAME

BACKGROUND

Technical Field

The present disclosure relates to a surgical system and method of use of the same. More particularly, the present disclosure relates to a self-optimizing laser surgical system including a laser scalpel that utilizes photon density waves to evaluate tissue of interest and adjust the intensity level output of the laser scalpel to an optimal setting for a specific tissue site.

Description of Related Art

The use of laser surgical systems that employ laser scalpels to treat tissue is well established. In a typical laser scalpel, a laser beam is emitted from the scalpel tip and a small focal spot of concentrated laser light energy cuts tissue by local burning or vaporizing at the focal spot. The scalpel tip itself, typically, does not contact the tissue being cut.

The surgeon relies on experience, judgment and technique to determine an intensity level of a laser beam that is to be applied to tissue of interest to achieve a desired tissue effect. Unfortunately, however, characteristics of tissue are not "static." That is, characteristics of tissue may differ from patient to patient, and/or site to site within a particular patient. For example, tissue associated with a liver of one patient may have characteristics associated therewith that are different than tissue associated with a liver of a different patient. As a result thereof, it is sometimes difficult for a surgeon to determine an appropriate intensity level of the laser beam to treat tissue. As can be appreciated, the efficacy at which a surgeon can utilize conventional laser surgical system with respect to treating tissue may be compromised and/or diminished by the "dynamic" nature of tissue.

SUMMARY

In view of the foregoing, it may prove advantageous to provide a self-optimizing laser surgical system including a laser scalpel that utilizes photon density wave to evaluate tissue of interest and adjust the intensity level output (and in certain instances a modulated frequency) of the laser scalpel to an optimal setting for a specific tissue site.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

In accordance with the instant disclosure, as used herein, treating tissue may include, but is not limited to dissecting, coagulating, ablating or cutting tissue.

An aspect of the present disclosure provides a surgical system for treating tissue. The surgical system includes a laser. A laser scalpel may be adapted to couple to the laser source and may be operable in two modes of operation, a first mode of operation to analyze tissue of interest and a second mode of operation to treat tissue of interest. The laser scalpel may include a housing having first and second fiber optic cables extending therethrough. Each of the first and second fiber optic cables may be operable under the first mode of operation to collect information pertaining to at least one optical property of tissue of interest and the second fiber optic cable also operable under the second mode of operation to treat the tissue of interest. The laser scalpel may be a carbon dioxide laser scalpel configured to ablate, coagulate or cut tissue.

A switching mechanism may be disposed on either the laser scalpel or the laser source and may be configured to place the laser scalpel in the first and second modes of operation.

In the first mode of operation the second fiber optic cable emits a modulated signal at a frequency (e.g., a frequency between 50 MHz to 3 GHz) capable of producing resolvable photon density waves to propagate through the tissue of interest and the first fiber optic cable receives information pertaining to the photon density waves. In this instance, the information pertaining to the photon density waves may be utilized to calculate the at least one optical property of tissue of interest. The at least one optical property of tissue of interest may be scattering and/or absorption properties of tissue.

One or more control algorithms may be associated with a microprocessor of the laser source and utilize the scattering and absorption properties of the tissue of interest to determine one of an energy output of the laser scalpel, frequency of the laser scalpel, duration of the laser pulses emitted from the laser scalpel, type of waveform utilized by the laser scalpel and duty cycle of the laser scalpel.

The first and second fiber optic cables may extend to a distal face of the housing and may include respective polished end-faces that are positioned flush with the distal face of the housing and bulged to create a rounded projection to enhance contact with tissue of interest. The first and second fiber optic cables may be positioned in vertical registration with respect to one another and spaced-apart from each other at a distance that ranges from about 7 mm to about 10 mm. The first optical fiber may include a diameter that ranges from about 700 microns to about 1 mm and the second optical fiber includes a diameter that ranges from about 200 microns to about 400 microns.

An aspect of the present disclosure provides a method for treating tissue. A laser surgical system including a laser source and a laser scalpel adapted to couple thereto is provided. The laser scalpel is positioned adjacent tissue of interest. The laser scalpel is activated to function in a first mode of operation to analyze the tissue of interest. The laser scalpel is activated in the second mode of operation to treat the tissue of interest, e.g., cut, coagulate or ablate tissue.

The laser scalpel may be provided with a housing having first and second fiber optic cables extending therethrough. Each of the first and second fiber optic cables may be operable under the first mode of operation to collect information pertaining to at least one optical property of tissue of interest and the second fiber optic cable is also operable under the second mode of operation to treat the tissue of interest. The laser scalpel may be provided with a switching mechanism configured to place the laser scalpel in the first and second modes of operation. The first and second fiber optic cables may extend to a distal face of the housing, wherein the first and second fiber optic cables include respective polished end-faces that are positioned flush with the distal face of the housing and bulged to create a rounded projection to enhance contact with tissue of interest.

A modulated signal may be emitted from the second fiber optic cable at a frequency (e.g., a frequency between 50 MHz to 3 GHz) capable of producing resolvable photon capable of causing photon density waves to propagate through the tissue of interest such that the first fiber optic cable receives information pertaining to the photon density waves.

At least one optical property associated with the tissue of interest may be calculated from the information pertaining to the photon density wave, wherein the at least one optical property of tissue of interest is scattering and absorption properties of tissue of interest.

The laser source may be provided with at least one microprocessor and control algorithm that utilizes the scattering and absorption properties of the tissue of interest to determine one of an energy output of the laser scalpel, frequency of the laser scalpel, duration of the laser pulses emitted from the laser scalpel, type of waveform utilized by the laser scalpel and duty cycle of the laser scalpel.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As noted above, characteristics of tissue are dynamic and not static and, as a result thereof, it is sometimes difficult to determine an appropriate intensity level of a laser beam needed to effectively treat tissue of interest. In accordance with the instant disclosure, it has been found that utilizing one or more optical properties associated with tissue of interest allows a user to effectively treat tissue of interest irrespective of the patient and/or type of tissue.

Figure 1:
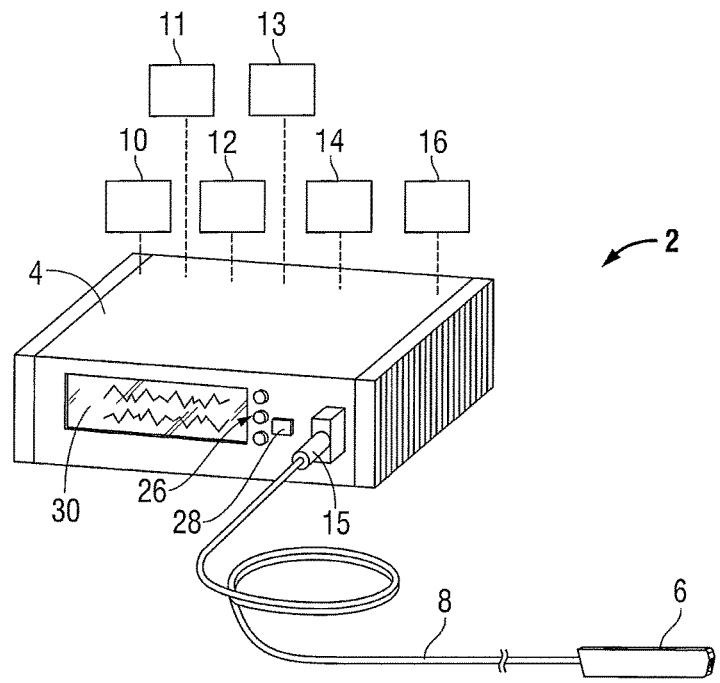
FIG. 1 is a perspective view of a self-optimizing laser surgical system including a laser source and laser scalpel according to an embodiment of the present disclosure.

Turning now to FIG. 1, a self-optimizing laser surgical system 2 including a laser source 4 and a laser scalpel 6 configured to treat tissue is illustrated. In accordance with the instant disclosure, laser source 4 is operable in two modes of operation, a first mode of operation to analyze tissue of interest and a second mode of operation to treat tissue of interest. To these ends, laser source 4 may include one or more microprocessors 10 that are in operative communication with one or more modules, e.g., a digital signal processing module 12 (DSP 12), of the laser source 4. Processor 10 receives command signals from DSP 12 and regulates one or more parameters associated with a laser beam, e.g., an intensity level of a laser beam, emitted from the laser scalpel 6. DSP 12 may be in operable communication with a detector 11 that may be in the form of a photon multiplier tube, avalanche photo diode, or photodiode. A laser driver 13 may be utilized to modulate the laser to a desired frequency. A read only memory 14 (ROM 14) may store one or more control algorithms configured to determine absorption and scattering properties of tissue of interest based on information collected from the laser scalpel 6 at a tissue treatment site and transmitted to the DSP 12. The DSP 12 and/or the at least one control algorithm may utilize the scattering and absorption properties of the tissue of interest to determine and/or adjust an intensity level of a laser beam emitted from the laser scalpel, frequency of the laser beam emitted from the laser scalpel, duration of the laser pulses of the laser beam emitted from the laser scalpel, type of waveform utilized by the laser scalpel and duty cycle of the laser scalpel.

A driving circuit 16 (FIG. 1) in operable communication with the processor 10 is provided with the laser source 4 and may include one or more light sources (not explicitly shown) configured to generate light at one or more wavelengths. By way of example, the light sources of the driving circuit 16 may be laser diodes (or other suitable device(s)) that emit light with wavelengths of approximately 500 nm to about 2000 nm. By way of example, the light sources of the driving circuit 16 may be laser diodes (or other suitable device(s)) that emit light with wavelengths of approximately 800 nm to about 810 nm or a $CO_2$ laser at about 1060 nm.

Figure 2:
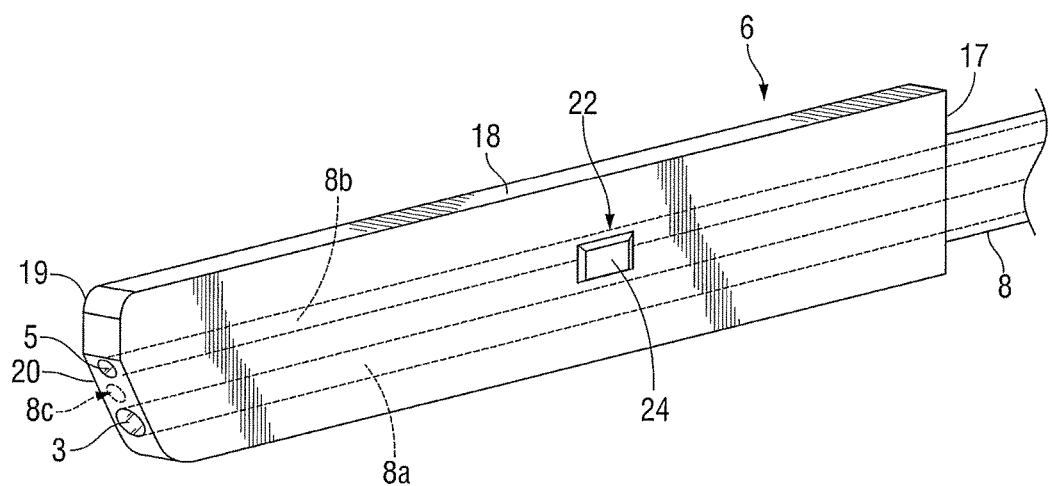
FIG. 2 is a perspective view of the laser scalpel depicted in FIG. 1.

A cable 8 connects the laser source 4 to the laser scalpel 6, and may include one or more fiber optic cables therein (FIGS. 1 and 2). Cable 8 may couple to the laser source 4 and laser scalpel 6 via one or more suitable coupling methods, e.g., via an optical connection 15, such as, for example, a fiber channel connector (FC connector) or a subscriber connector (SC connector) (not explicitly shown coupled to the laser scalpel 6), see FIG. 1. In the illustrated embodiment, cable 8 includes a first fiber optic cable 8a and a second fiber optic cable 8b (FIG. 2). Each of the first and second fiber optic cables 8a, 8b are operable under the first mode of operation to collect information pertaining one or more optical properties of tissue of interest, as described in greater detail below.

Referring to FIG. 2, laser scalpel 6 is illustrated. In the illustrated embodiment, the laser scalpel 6 holds the optics fibers that guide and emits one or more suitable lasers, e.g., a carbon dioxide (CO2) laser including a housing 18 having generally rectangular configuration. Other suitable configurations, however, may be utilized for the housing 18. Housing 18 may be made from any suitable material including, but not limited to metal, plastic, ceramic, surgical steel, etc. Housing 18 includes proximal and distal ends 17 and 19, respectively, and is configured to house the first and second fiber optic cables 8a, 8b therein (FIG. 2).

First fiber optic cable 8a extends through a housing 18 of the laser scalpel 6 and includes a distal tip 3 that is disposed flush with a distal face 20 of the housing 18 (FIG. 2). In some embodiments, distal tip 3 may be polished to facilitate positioning the distal tip 3 flush with the distal face 20. In another embodiment, distal tip 3 may be polished and bulged to create a rounded projection that can enhance contact with tissue. In either of the aforementioned embodiments, positioning the first fiber optic cable 8a flush with the distal face 20 facilitates collecting information, e.g., optical information, pertaining to the tissue of interest. First fiber optic cable 8a may include any suitable diameter. In embodiments, the diameter of the first fiber optic cable may range from about 700 microns to about 1 mm.

First fiber optic cable 8a is operable under the first mode of operation to collect information pertaining to one or more optical properties of tissue of interest. In particular, the first fiber optic cable 8a receives information pertaining to photon density waves (PDW). More particularly, the first fiber optic cable 8a receives resolvable amplitude and phase relationships of the PDW. The information pertaining to the PDW is communicated to the DSP 12 for processing and utilized by the control algorithm to calculate one or more optical properties, e.g., scattering and absorption properties, of tissue of interest. In particular, the control algorithm utilizes the phase of the PDW which is sensitive to the scattering coefficient associated with the tissue of interest, and the amplitude of the PDW which is sensitive to the concentrator of the absorber in the tissue of interest to determine an appropriate intensity level and frequency of the laser output for the second mode of operation. In certain embodiments, the first fiber optic cable 8a may also be operable in the second mode of operation.

Continuing with reference to FIG. 2, second fiber optic cable 8b is illustrated. Second fiber optic cable 8b extends through housing 18 and includes a distal tip 5 that is disposed flush with the distal face 20. In some embodiments, distal tip 5 may be polished to facilitate positioning the distal tip 5 flush with the distal face 20. In another embodiment, distal tip 3 may be polished and bulged to create a rounded projection that can enhance contact with tissue. In the illustrated embodiment, second fiber optic cable 8b is positioned in vertical registration with respect to first fiber optic cable 8a. Other positioning configurations, however, of the first and second fiber optic cables 8a, 8b may be utilized. For example, in certain embodiments, the first and second fiber optic cables 8a, 8b may be positioned in horizontal registration with one another. First and second fiber optic cables may be spaced-apart from one another at any suitable distance. The distance that separates the first and second fiber optic cables 8a, 8b from one another affects a penetration depth of the PDW through tissue. The depth of penetration of the PDW is directly proportional to the distance that separates the first and second fiber optic cables 8a, 8b, i.e., the greater the distance, the greater the penetration depth of the PDW through tissue. In one particular embodiment, for example, first and second fiber optic cables 8a and 8b may be spaced-apart from each other at a distance that ranges from about 7 mm to about 10 mm. It has been found that this range is sufficient for analyzing a top layer of tissue of interest.

Second fiber optic cable 8b is operable under the first mode of operation. In particular, second fiber optic cable 8b emits a modulated signal provided by one or more modules or components, e.g., the light source and a modulator (not explicitly shown), of the laser source 4 at a frequency capable of producing distinguishable PDW to propagate through the tissue of interest. It has been found that a modulated signal having a frequency that ranges from about 50 MHz to about 3 GHz is capable of producing distinguishable PDW to propagate through the tissue of interest with meaningful phase and amplitude information.

Unlike first fiber optic cable 8a, however, second fiber optic cable 8b is also operable under the second mode of operation to treat the tissue of interest. To this end, second fiber optic cable 8b includes a diameter that is less than the diameter of the first fiber optic cable to provide a small focal "spot" of concentrated energy at the tissue site. In embodiments, the second fiber optic cable 8b may include a diameter that ranges from about 200 microns to about 400 microns. It has been found that fiber optic cables having diameters close to the 400 micron range can provide laser beams with intensity levels of up to 20 watts, which is suitable to treat tissue of interest in accordance with the instant disclosure.

With reference again to FIG. 2, one or more switching mechanisms 22 may be provided on the laser source 4 and/or laser scalpel 6 and utilized to place the laser scalpel 6 in the first and second modes of operation. In the illustrated embodiment, the switching mechanism 22 is provided on an exterior surface of the housing 18 of the laser scalpel 6. The switching mechanism 22 may be any suitable type of switching mechanism. In some embodiments, such as the illustrated embodiment, the switching mechanism 22 may be an analog push-button switch 24 (FIG. 2). The analog push-button switch 24 is configured to communicate with the microprocessor 10 to place the laser scalpel 6 in the first and second modes of operation.

One or more visual indicators 26 may be provided on the laser scalpel 6 and/or laser source 4 to indicate to a user that the laser scalpel 6 is ready for operation in one of the first and second modes of operation (FIG. 1). For example, one or more light emitting diodes (LEDs) or the like may be provided on the laser source 4 and configured to illuminate when the laser scalpel 6 is ready to operate in one of the first and second modes of operation. Alternatively, or in combination therewith, one or more speakers 28 (FIG. 1) may be provided on the laser source 4 and/or laser scalpel 6 and configured to provide a beep or tone of suitable frequency when the laser scalpel 6 is ready to operate in the first and second modes of operation.

In certain embodiments, the switching mechanism 22 may be configured to illuminate in one or more colors that indicate a specific mode of operation of the laser scalpel 6, e.g., whether the laser scalpel 6 is in the first or second mode of operation.

In operation of one particular embodiment, a user may position the distal face 20 of the laser scalpel 6 adjacent tissue of interest, e.g., flush against tissue of interest. Thereafter, a user may press the push-button switch 24 to place the laser scalpel 6 in the first mode of operation to initiate an optical property analysis of the tissue of interest, e.g., a top layer of the tissue of interest. In one particular embodiment, the push-button 24 stays illuminated in a first color, e.g., red, during the first mode of operation.

In the first mode of operation, laser source 4 transmits a modulated signal that is emitted from the second fiber optic cable 8b to cause resolvable PDW to propagate through the tissue of interest. Moreover, the first fiber optic cable 8a receives the pertinent information relating to tissue of interest, e.g., resolvable amplitude and phase relationships of the PDW, and communicates this information to the DSP 12 to be implemented by the control algorithm.

Thereafter, a control signal is transmitted from the DSP 12 to the microprocessor 10, which, in turn, sets (or in certain instances adjusts) one or more of the aforementioned parameters associated with the laser scalpel 6, e.g., an intensity level of the laser beam emitted from the laser scalpel 6, to an appropriate level.

Subsequently, one or more of the aforementioned indicators, e.g., visual indicators 26, may be automatically activated (e.g., by the microprocessor) to indicate to a user that the optical analysis of tissue of interest is complete and the laser scalpel 6 is ready to operate in the second mode of operation. A user may then press push-button 24 to begin treatment of tissue of interest. In one particular embodiment, the push-button 24 stays illuminated in a second color, e.g., blue, during the first mode of operation.

The self-optimizing laser surgical system 2 overcomes the drawbacks that are typically associated with conventional laser surgical systems. In particular, the self-optimizing laser surgical system 2 provides a user with an efficient method for treating tissue of interest irrespective of the patient and/or type of tissue. That is, self-optimizing laser surgical system 2 adjusts one or more of the aforementioned characteristics of the laser beam based on the scattering and absorption properties of tissue to treat tissue.

From the foregoing and with reference to the various figure drawings, those skilled in the art will appreciate that certain modifications can also be made to the present disclosure without departing from the scope of the same. For example, a footswitch (not explicitly shown) may be provided in addition to or instead of the push-button 24 to control the laser scalpel 6.

One or more monitors 30 (FIG. 1) may be provided on the laser source 4 and configured to provide relevant information pertaining to the laser source 4 and/or laser scalpel 6. The relevant information may include power intensity of the laser beam emitted from second fiber optic cable 8b, duration of duty cycle of laser scalpel 6, etc.

In certain embodiments, a third fiber optic cable 8c may be provided and configured to function as one or both of the first and second fiber optic cables 8a, 8b. For example, and in one particular embodiment, during the first mode of operation, the third fiber optic cable 8c may be configured to receive resolvable amplitude and phase relationships of the PDW. Or, during the first mode of operation, the third fiber optic cable 8c may be configured to emit a modulated signal to produce resolvable PDW to propagate through tissue of interest.

In some embodiments, it may prove advantageous for both the first and second fiber optic cables 8a, 8b to treat tissue. For example, and in one particular embodiment, the first fiber optic cable 8a may be configured to treat tissue with a first laser beam having a particular intensity, waveform, duty cycle, etc., and the second fiber optic cable may be configured to treat tissue with a second laser beam having a particular intensity, waveform, duty cycle, etc. that is different from the first laser beam. This embodiment may prove advantageous in the instance where multiple tissue of interest needs to be treated.

In certain embodiments, it may prove advantageous to provide a laser scalpel 6 with a single fiber optic cable, e.g., second fiber optic cable 8b, that is configured to both analyze and treat tissue of interest. In this particular embodiment, the second fiber optic cable 8b, for example, emits a modulated signal into the tissue of interest and detects a phase shifted return signal therefrom that contains the pertinent information relating to the PDW. Thereafter, the second fiber optic cable 8b emits the laser beam to treat tissue of interest. As can be appreciated, one or more modules and/or components, e.g., a DSP 12 having phase delay capabilities, may be added to the laser source 4 to accommodate for this specific configuration of the fiber optic cable 8b.

Additionally, while the laser surgical system 2 has been described as utilizing a laser scalpel 6 that utilizes CO2 gas, other embodiments may include a laser scalpel 6 that utilizes Helium-Neon (HeNe) gas or Argon (Ar) gas. Moreover, other embodiments may include a laser scalpel 6 that utilizes a combination of one or more suitable metals, solid state and gases, such as, for example, Neodymium-doped Yttrium Aluminium Garnet (Nd:YAG), Helium-Silver (HeAg) and Neon-Copper (NeCu).

Further, while laser scalpel 6 has been described as a "gas" type laser, other embodiments may include laser scalpels 6 that are chemical lasers, solid state lasers, photonic lasers, semiconductor lasers, dye lasers, bio lasers, etc.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical system for treating tissue, comprising:
  a laser source;
  a laser scalpel adapted to couple to the laser source and operable in a first mode of operation to analyze tissue and a second mode of operation to treat the tissue, the laser scalpel including a housing, the housing defining a longitudinal axis and including:
    a first pair of opposing planar surfaces defining a length of the housing;
    a second pair of opposing planar surfaces separating the first pair of opposing planar surfaces, the second pair of opposing planar surfaces defining a thickness of the housing;
    a switch in communication with the laser source and extending from one of the first pair of opposing planar surfaces, the switch configured to be pressed relative to the housing to selectively place the laser scalpel in one of the first or second mode of operation;
    a planar first distal face;
    a planar second distal face configured to contact the tissue; and
    a chamfered third distal face extending proximally from a first linear edge of the first distal planar face to a distal end of one of the first pair of opposing planar surfaces, the second distal face extending proximally from a second linear edge of the first distal face to a distal end of the other of the first pair of opposing planar surfaces and disposed at an oblique angle relative to the longitudinal axis defined by the housing, each of the first, second, and third distal faces disposed between the first pair of opposing planar surfaces; and
  first and second fiber optic cables extending through the housing to the planar second distal face and each of the first and second fiber optic cables including a distal tip bulged from the planar second distal face to create a rounded projection extending from the planar second distal face, each of the first and second fiber optic cables operable in the first mode of operation to collect information pertaining to at least one optical property of tissue, and at least one of the first or second fiber optic cables also operable in the second mode of operation to treat tissue, the first fiber optic cable configured to receive amplitude and phase information of a resolvable photon density wave generated through tissue by the second fiber optic cable during the first mode of operation, the laser source including a processor configured to:
    utilize the amplitude information to determine a concentrator of an absorber in the tissue;
    utilize the phase information to determine a scattering coefficient of the tissue; and
    control an intensity level and frequency of a laser beam emitted from the laser scalpel during the second mode of operation based on the determined concentrator of the absorber in the tissue and the determined scattering coefficient of the tissue,
  wherein the first and second fiber optic cables are positioned in vertical registration with respect to one another and spaced-apart from one another at a distance that ranges from about 7 mm to about 10 mm.

2. A surgical system according to claim 1, wherein in the first mode of operation, the second fiber optic cable emits a modulated signal at a frequency capable of producing resolvable photon density waves to propagate through the tissue and the first fiber optic cable receives information pertaining to the photon density waves, and in the second mode of operation the second fiber optic cable is operable to treat the tissue.

3. A surgical system according to claim 1, wherein the first optical fiber includes a diameter that ranges from about 700 microns to about 1 mm and the second optical fiber includes a diameter that ranges from about 200 microns to about 400 microns.

4. A surgical system according to claim 1, wherein the laser scalpel is a carbon dioxide laser scalpel.

5. A surgical system according to claim 1, wherein at least one of the first or second fiber optic cables are operable to one of ablate or coagulate the tissue when the laser scalpel is in the second mode of operation.

6. A surgical system according to claim 1, further comprising a third fiber optic cable extending through the housing to the planar second distal face of the housing and including a distal tip bulged from the planar second distal face of the housing to create a rounded projection extending from the planar second distal face.

7. A surgical system according to claim 6, wherein the third fiber optic cable is configured to function as one or both of the first and second fiber optic cables and configured receive resolvable amplitude and phase relationships of photon density waves.

8. A surgical system for treating tissue, comprising:
a laser source;
a laser scalpel adapted to couple to the laser source and operable in a first mode of operation to analyze tissue and a second mode of operation to treat the tissue, the laser scalpel including a housing, the housing defining a longitudinal axis and including:
a first pair of opposing planar surfaces defining a length of the housing;
a second pair of opposing planar surfaces separating the first pair of opposing planar surfaces, the second pair of opposing planar surfaces defining a thickness of the housing;
a push-button switch in communication with the laser source and extending from one of the first pair of opposing planar surfaces, the push-button switch configured to be pressed relative to the housing to selectively place the laser scalpel in one of the first or second mode of operation;
a planar first distal face;
a planar second distal face configured to contact the tissue; and
a chamfered third distal face extending proximally from a first linear edge of the first distal planar face to a distal end of one of the first pair of opposing planar surfaces, the second distal face extending proximally at an oblique angle relative to the longitudinal axis from a second linear edge of the first distal face to a distal end of the other of the first pair of opposing planar surfaces; and
first and second fiber optic cables extending through the housing to the planar second distal face, each of the first and second fiber optic cables operable in the first mode of operation to collect information pertaining to at least one optical property of tissue, and at least one of the first or second fiber optic cables also operable in the second mode of operation to treat tissue.

* * * * *